United States Patent
Schmidt

Patent Number: 6,122,537
Date of Patent: Sep. 19, 2000

[54] METHOD OF AND APPARATUS FOR DETECTING VITAL FUNCTIONS OF LIVING BODIES

[75] Inventor: Gerd Juergen Schmidt, Frankfurt am Main, Germany

[73] Assignee: Selectornic Gesellschaft fur Sicherheitstechnik und Sonderelektronik mbH, Germany

[21] Appl. No.: 08/676,321
[22] PCT Filed: Jan. 20, 1995
[86] PCT No.: PCT/DE95/00065
   § 371 Date: Jan. 12, 1997
   § 102(e) Date: Jan. 12, 1997
[87] PCT Pub. No.: WO95/20171
   PCT Pub. Date: Jul. 27, 1995

[30] Foreign Application Priority Data

Jan. 20, 1994 [DE] Germany ............ 94 00 950 U

[51] Int. Cl.[7] .......................................... A61B 5/05
[52] U.S. Cl. .................. 600/407; 600/484; 600/534
[58] Field of Search ................... 600/407, 300, 600/301, 481, 529, 483, 508, 484, 534

[56] References Cited

U.S. PATENT DOCUMENTS

| 3,796,208 | 3/1974 | Bloice | 600/534 |
| 3,815,131 | 6/1974 | Dautel et al. | 340/258 |
| 4,958,638 | 9/1990 | Sharpe et al. | 600/407 |
| 5,305,748 | 4/1994 | Wilk | 600/407 |

FOREIGN PATENT DOCUMENTS

2645307  4/1989  France .

OTHER PUBLICATIONS

Y. Lipkin et al., "Microwave Repiration Monitor", 1979 Carnahan Conference on Crime and Countermeasures, pp. 53–56, May 16–18, Lexington, Kentucky, May 1979.

*Primary Examiner*—Brian L. Casler

[57] ABSTRACT

An apparatus for detecting vital functions of living bodies by means of electromagnetic signals includes a receiving device for electromagnetic signals. The receiving device for electromagnetic signals includes a device for obtaining frequency components that are characteristic of living bodies, out of received electromagnetic signals. The receiving device includes a direct demodulator that has a non-linear current/voltage characteristic that is frequency-selective for demodulation of frequency components that are characteristic of living bodies.

27 Claims, 9 Drawing Sheets

STRUCTURE OF THE EVALUATION CHAIN

Frequency: 1.221481   Value: 5276.754

METHOD OF AND APPARATUS FOR DETECTING VITAL FUNCTIONS OF LIVING BODIES

BACKGROUND OF THE INVENTION

Field of the Invention

The invention concerns an apparatus for detecting vital functions of living bodies, and more particularly to an apparatus for detecting vital functions of living bodies by means of electromagnetic signals.

The inventors found that living bodies and therefore also human living bodies surprisingly influence high-frequency electromagnetic signals by virtue of their most important vital functions, that is to say their heartbeat and their respiration activity.

Those vital functions generally take place within known frequency ranges, which with the human heart rate can be from about 0.5 through 3.4 Hz and normally are about 1 through 2 Hz and in the case of respiration can extend between 0.1 and 1.5 Hz. That defines characteristic frequency ranges. Upon the reception and recording of electromagnetic signals those frequency ranges are visible when people are in the reception region. In addition it is possible to provide information about the number of people located, on the basis of received and also processed signals. In that respect, use is made of the principle of biological variety and specificity, on the basis of which the heart and respiration frequency patterns of different people differ. For four or more people however, it is generally no longer possible clearly to distinguish between the number of people by virtue of the frequency superimposition of the respective frequencies. As from that number of people it is then only possible to provide the information that: there are at least four people present.

In any event a frequency range of 0.01 through 10 Hz includes all frequencies which are of interest in terms of the vital functions of a human body.

What was surprising was the realisation that even without emitted transmission power, just the receiver device together with the device for obtaining the frequency components which are characteristic of living bodies the inventors were in a position to provide the desired identification effect for the vital functions.

This means that the presence of a living body, at least in the vicinity of the receiver device, already results in detectable signal components in the specified frequency ranges, without in that respect the need for through-radiation with a carrier signal.

With the receiver device for electromagnetic signals and the device for obtaining frequency components which are characteristic in respect of living bodies, without additional emitted signals, the inventors were already in a position of reliably detecting living bodies at up to more than 3 meters distance or approximately the distance of the storey of a building.

In the simplest embodiment of the invention the direct demodulator described hereinafter, in the form of a diode direct receiver for receiving the frequency components which are characteristic in respect of living bodies, was already sufficient.

In addition transmitters were later used, with which through-radiation of the detection area was effected, and reflected, transmitted or scattered radiation was received, the investigation thereof for pronounced frequency components providing the proof of the presence of living bodies.

So that electromagnetic radiation can still be received through dense debris, even at some distance, frequencies of the electromagnetic radiation of some hundred megahertz to about 10 gigahertz were used, which ensured a high depth of penetration.

That radiation experienced phase modulation which added side bands displaced by some Hertz to the high-frequency carrier signal. With conventional reception procedures, detection of frequency bands which are so close together would have required short term-stable oscillators with deviations of less than $10^{-12}$, which hitherto was considered to be unattainable at reasonable cost. That problem is made more acute by the low levels of received signal powers.

Some of the advantages of the embodiments described herein are discussed hereinafter.

The use of known phase modulators initially appears obvious. Homodyne, heterodyne and PLL (Phase Locked Loop) methods and the excitation of the flanks of a local oscillation circuit are known. It has been found however that none of the foregoing processes was capable of supplying the desired results at an expenditure that was reasonable. It was only the use of a direct demodulator which permits direct separation of the modulation frequency from the modulated frequency, that leads to the desired results. It is assumed however that, with suitable apparatus expenditure and improved circuit arrangements, the foregoing methods can be used in accordance with the present invention.

With a component with a non-linear current/voltage characteristic as the frequency-selective element, it was possible to provide inexpensively and reliably for demodulation of the frequency components which are of interest. A diode, a bipolar or a field effect transistor could be successfully used as the element with a non-linear characteristic.

Those components are both inexpensively obtainable and also non-critical in regard to their use. The optimum working range of those components of from about 100 kHz to 200 MHz could be used at higher reception frequencies by means of a frequency conversion device connected upstream of the demodulator. Although that frequency conversion device added tolerable distortion in the time region to the signal, it did however superimpose only a slight amount of additional noise.

The signal to be received could be raised with a transmitter device for transmitting an electromagnetic carrier signal at a fixed frequency; however a very high level of attention had to be paid to the stability of the carrier frequency in order to exclude undesirable modulation effects in the frequency range which is of interest. A simple quartz-stabilised analog transmission circuit with an oscillator circuit of high quality surprisingly showed itself to be a suitable oscillator, after an adequate transient or build-up time.

The method and the apparatus according to the invention can also be used for object monitoring and/or safeguarding. The specific embodiments show, at a later point in this description, static monitoring arrangements.

The use of an analog sampling filter, unlike high-frequency digital filters, did not exhibit any detrimental additional frequency components and crucially contributed to the quality of the signal obtained. Additional undesirable signal components such as for example noise and superimposed interference were prevented by limiting the band width of the electromagnetic signal prior to the sampling operation and prior to A/D-conversion to high frequencies.

The use of an analog high pass filter for preventing low-frequency components in respect of the frequencydependent 1/f-noise of the transmission oscillator and internal structural units was also important.

The unexpectedly good operation of the apparatus according to the invention and the method according to the invention also permits use thereof in many areas.

People who are in danger of committing suicide can be monitored in psychiatry or in places of detention, without requiring constant inspection by personnel who are in charge of such people.

The invention is described in detail hereinafter by means of embodiments given by way of example with reference to the accompanying drawings in which:

DETAILED DESCRIPTION OF PREFERRED EMBODIMENTS

The invention is firstly described hereinafter more generally and then in greater detail with reference to individual embodiments.

Figure 1:
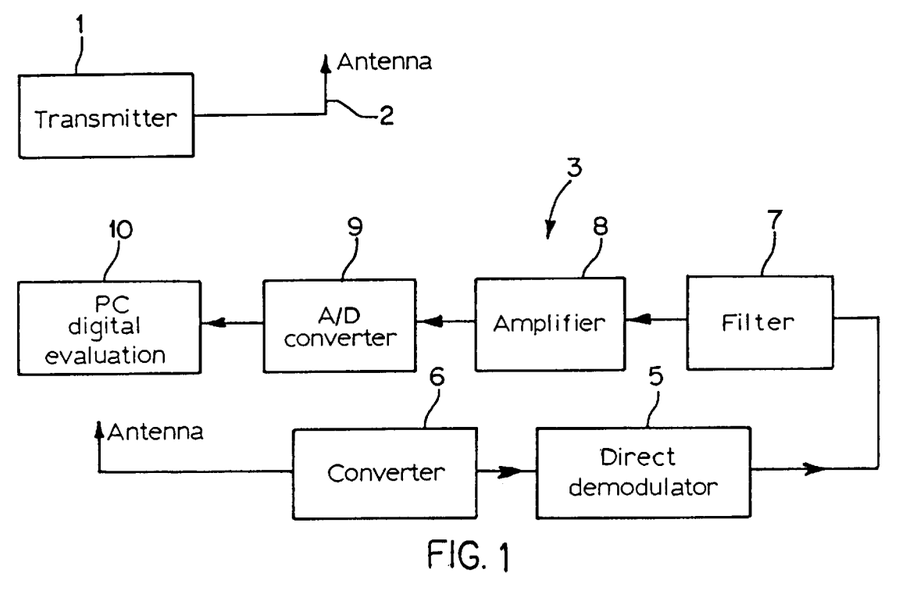
FIG. 1 is a diagrammatic view of the main units of an embodiment of the apparatus according to the invention.

FIG. 1 shows an arrangement with a transmitter 1 and a transmission antenna 2 which transmit at a fixed frequency which is preferably in the range of some 100 MHz through about 10 GHz.

The transmission antenna 2 preferably has a lobe-shaped fixed directional characteristic. Depending on the respective embodiment of the invention the transmitter 1 and the antenna 2 are in the form of a portable unit or are mounted stationary.

Figure 2:
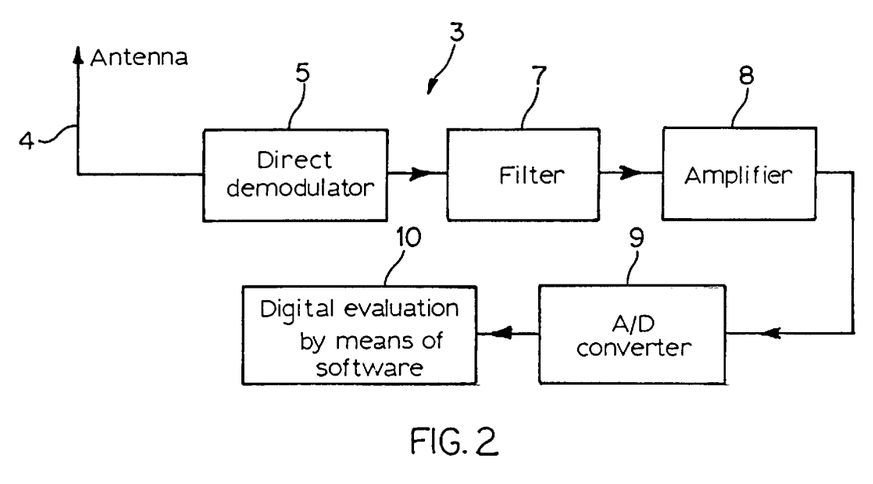
FIG. 2 is a diagrammatic view of a simpler embodiment of the apparatus according to the invention with the main components thereof.

The receiver device which is generally identified by reference 3 and which is shown in a simpler embodiment in FIG. 2 includes a receiving antenna 4 connected to a direct demodulator 5 which, from the received electromagnetic signal, demodulates the frequency components which are characteristic of living bodies. That demodulation effect is performed in the form of phase or frequency demodulation and can already provide the desired frequency components at the output of the direct demodulator 5.

Figure 7:
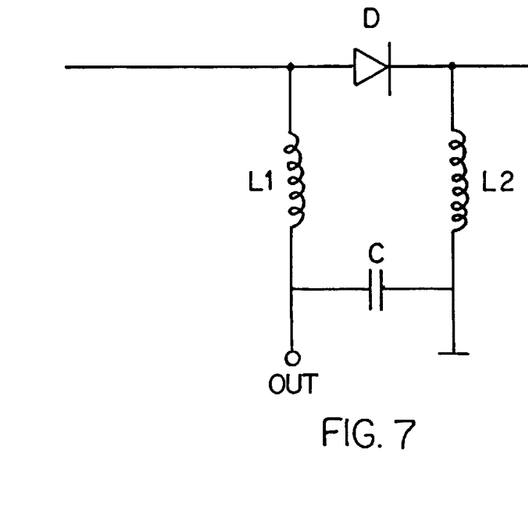
FIG. 7 shows a diode direct receiver without converter connected upstream thereof.

In comparison with the embodiment of the direct demodulator shown in FIG. 7, it may also comprise a rectifier bridge of known kind which results in a voltage-doubled or voltage-multiplied useful signal.

In a further configuration, the receiving device 3 includes a frequency conversion device 6 which is connected upstream of the demodulator 5 and which as a converter converts signals received above about 200 megahertz to terahertz into frequency ranges in which the direct demodulator 5 has increased reception powers. When using diodes, a bipolar or a field effect transistor, that suitable, downwardly converted optimum working range is at about 100 kHz through 200 MHz.

Connected downstream of the direct demodulator is a filter device 7 for filtering out undesired signal components, which limits the band width of the electromagnetic signal, prior to the sampling operation (prior to the analog/digital conversion operation), towards high frequencies. That filter device 7 also limits the band width towards low frequencies. The amplifier 8 connected downstream of the filter 7 increases the voltage or in an alternative configuration the current of the received signals and passes it for sampling to an analog/digital converter 9.

After analog/digital conversion the frequency components which are characteristic of living bodies are processed by a computer device 10 for spectral analysis and spectrally represented. In that case the intensity of the frequency components which are characteristic of living bodies gives information about the presence of the vital functions of the human bodies detected.

In the event of evaluation of the signals in respect of time, the digital signal, for removing distortion thereof, is folded or convoluted with the inverse transfer function of the receiving device 3.

As reliable detection of those signals is extremely difficult, the direct receiver with the non-linear element will be described hereinafter, on the basis of a diode direct receiver.

Diode direct receiver

The reflected signal is phase or frequency modulated. Detection of that modulation is not possible, or is possible only with extreme difficulties, with the usual reception procedures for FM (frequency modulation) and PM (phase modulation). So that a signal which is phase modulated with 0.2 Hz can be detected, for example with 10 GHz, accurately to 0.2±0.02 Hz, short term-stable synchronised oscillators with deviations of less than $10^{-12}$ would be necessary. That seemed hitherto unattainable from a technical point of view.

A way of directly detecting the modulation of the received signal was therefore sought.

Suitable for that purpose are for example components with mostly quadratic characteristics; they are inter aha field effect transistors, components with exponential characteristics which in a portion-wise manner can be approximated as quadratic, diodes and transistors. If now the sum of two frequencies is applied as the impressed, received voltage, that results in higher-order terms.

If there is a quadratic term, difference frequencies also occur, beside the rectified current. In order to demodulate the phase-modulated signal which is reflected by the person to be detected, a conventional rectifier can thus already surprisingly be used, in spite of the very high requirements in regard to frequency behaviour.

The phase-modulated signal is impressed on the non-linear characteristic, and that results in currents which are proportional to the phase modulation frequency Ω and the multiples thereof k*Ω. The curve shape of the modulation is not retained, in consideration of the demodulation principle, but it has been found that those changes in the curve shape are not critical for most uses according to the invention as detection of the modulation can be sufficient for such uses.

The signal-noise ratio determines the sensitivity limit, in the case of direct detection. For the respiration rate, SN values of over 46 dB were achieved, while for the heart rate, values of 26 dB were achieved at a distance of 3 mm and with oscillator powers of about 5 nW.

On the assumption that the heart emits spherical waves, between the transmission and reception powers, there is a relationship which is inversely proportional to the second power of the distance. Therefore, for the ratio of the amplitudes of the respiration rate UA to the noise UN or the heart rate UH to the noise, it is possible to estimate that the reception limit with a transmission power of 1 W is then at about 50 m in relation to the heartbeat and at typically 160 m in relation to respiration.

Antennae with a higher gain and low-noise components can correspondingly increase those values in accordance with the invention. That means that sufficient reception signals are still to be expected in the location operation, even for ground layers of several meters thickness.

The diode which is ideal in terms of saturation current IO and temperature voltage is the Si power diode IN4004 whose suitability as a rectifier is however limited to high frequencies due to the high barrier layer capacitance. After that follows the low-signal Si diode IN4148, then the Si Schottky diode BAT46 and finally the two Ge diodes AA116 and AA144.

A diode direct receiver was respectively adjusted for 440 MHz 1.3 GHz, 2.4 GHz, 5.6 GHz and 10 GHz. For 4 of the 5 frequencies, receiving antennae were designed with a direct diode receiver:

440 MHz: half-wave dipole with v=0.940, Z=60.5 Ω and BAT 46

1.3 GHz: half-wave dipole with v=0.906, Z=57.4 Ω and BAT 46

2.4 GHz: half-wave dipole with v=9.40, Z=60.5 Ω and BAT 46

5.6 GHz: full-wave multi-wire triadic dipole with v=0.73, Z=140 Ω and BAT 46.

It was already found with that receiver that the level of sensitivity fell greatly, relative to the 2.4 GHz receiver. At 10 GHz, it was no longer possible to detect a usable voltage so that the construction of a 10 GHz diode direct receiver was abandoned. The available diodes no longer exhibited any usable rectifier effect at high frequencies of that kind.

As signals according to the invention can be graded by experts as being below the measurement limit, great attention has been paid to the types of antenna used.

Antennae

The front-back ratio must be made as large as possible, for the location procedure, in order to receive signals which are incident in opposite relationship to the main emission direction. Secondary lobes must also be minimized for that reason. Therefore the entire radiation diagram should have a main lobe which is as narrow as possible and no secondary lobes.

The input impedance of the antennae can and should be adapted in accordance with the invention to real or complex impedances in such a way that power adaptation is achieved in the case of transmitters and noise adaptation is achieved in the case of receivers. The fulfillment of those requirements by an antenna design is however not possible at the same time.

All antennae used are endfire antennae because backfire antennae of comparable dimensions always have a worse front-back ratio because the waveguide structure must be excited in the rearward direction. The antennae should be as wide-band as possible as an adjusting operation should not be involved. Logarithmically periodic structures are known as wide-band antennae with a very good front-back ratio. A wide-band nature on the one hand and a pronounced directional effect on the other hand are achieved by virtue of the logarithmic gradation of the waveguide structures. The fact that the gain, compared to resonant antennae of comparable dimensions, is lower, is generally not a problem for the situation of use according to the invention.

The polycone antenna can replace the rotational paraboloid antenna as deviations from the paraboloid configuration which are less than a tenth of a wavelength do not have an adverse effect on the performance of the antenna. Even at a fifth of the wavelength, the loss of amplification is below 2 dB and can thus be disregarded for most cases.

The design configuration of the paraboloid reflector, which is technically difficult to achieve, can thus be replaced by the polycone reflector which is easier to produce, without suffering disadvantages. The feed is however comparably expensive and complicated and the front-back ratio is only improved with reflectors which are large relative to the wavelength and whose illumination is limited to the inner region.

In order to overcome the problems involved in polarisation, in our embodiments with the two higher frequencies (5.6 GHz and 10.368 GHz) a circularly polarised antenna was used in each case, on the one hand as the receiving antenna and on the other hand as the transmitting antenna. Although admittedly that certainly gave rise to losses of typically 3 dB, they however are small in comparison with the losses which can occur in the case of mutually rotated, linearly polarised antennae.

In one embodiment with only one common transmitting/receiving antenna, the incoming and outgoing waves could be successfully separated, by means of a circulator.

Particular attention is also paid to the high-frequency units, in consideration of the difficult conditions to be overcome in terms of measurement procedure.

High-frequency units

The high-frequency units required are set forth hereinafter. The arrangement takes account of the possible links which occur between the modules and the peripheral elements. They correspond to the configurations according to the invention which we designed.

The direct modulators are used at the higher frequencies, that is to say at frequencies above about 200 MHz, after the converters which convert to the intermediate frequency of 137.5 MHz. Both the diodes used and also the transistors are operational at that frequency.

1. Diode mixer

The diode mixer comprises a symmetrical voltage multiplication circuit with a resonance circuit at the input and a low pass filter at the output.

Here, in contrast to the voltage which can be achieved when using a diode as the direct receiver, it is possible to achieve the quadruple output voltage as the sources are now connected in series. The increased internal resistance which is caused thereby is immaterial in terms of function.

In practical operation it was found that the diode mixer is superior, in regard to the signal-noise ratio, to the other known mixer designs.

Low-frequency units

All modules which are operated in the low-frequency range are equipped with their own power supply. That purpose is served by using individual lead accumulators of 12 V/2Ah which are provided with a voltage monitoring circuit and an on switch. Strict separation of all power supply units was found to be necessary as the use of a mains unit already resulted in considerable interference and trouble.

The entire arrangement is thus completely insulated on the transmitter side and on the receiver side it is only connected to the mains by way of the personal computer which however is in the form of a battery-powered unit in the case of portable apparatuses.

1. Pre-amplifier

The pre-amplifier uses a low-noise quadruple operational amplifier. One of the amplifiers is connected as an operating voltage symmetrising means; the other three are connected as band pass filters and are coupled together by way of high pass filters.

A low pass filter limits the noise of the first stage. By means of an optional resistor, it was possible for the diode direct receiver to be supplied with a preconduction current from the pre-amplifier. Overall two pre-amplifier modules with different levels of gain were used. As the sensitivity of the entire arrangement can result in overdriving of the A/D converter and thus a data loss, a regulated amplifier is necessary.

2. Sampling filter (anti-aliasing filter)

Sampling of time-dependent signals must be effected at a frequency which is greater than twice as high as the highest frequency contained in the input signal. Therefore the input signal must be spectrally limited prior to the analog-digital conversion step. Astonishingly, for the purposes of the present invention, that limitation operation must be effected by an analog filter and cannot be replaced by digital processing. If that is not taken into consideration, the situation involves sub-sampling of the spectral components which are above half the sampling frequency. They are mixed into the lower frequency range and irreversibly falsify the signal and therefore the success according to the invention cannot be achieved.

So-called digital anti-aliasing filters which lead the user to believe that band limitation can be effected after the A/D converter are surprisingly found to be completely ineffective in regard to the problem involved; all errors linked to sub-sampling occurred. Subsequent digital correction was no longer possible because of the destroyed signal content.

In general it is to be noted that among men skilled in the art, in regard to analog and digital parameters, there are false ideas such that the design of a measurement system for digital processing of analog parameters on the basis of the specifications of manufacturers and the exclusive use of the hardware and software offered thereby could not achieve the aim involved.

The requirements which are made in respect of the analog anti-aliasing low-pass filter are very high, depending on the respective further processing involved. Thus the dynamic range must be at least 1 bit better than that of the subsequent A/D converter and likewise linear and non-linear distortion effects must be at least 1 bit better than the A/D converter. Although the dynamic range of an N-bit A/D converter in practice is mostly only N−2 bits, those relationships must be borne in mind. The use of switch capacitor filters is possible if the sampling theorem is also taken into consideration in that respect and the dynamic range achieved is sufficient.

Folding or convolution of the input signal with the sampling filter results in amplitude and phase distortions and envelope curve distortions, on the basis of the group transit or delay time of the filter. Those signal changes can be taken into consideration if required by a procedure whereby the inverse transfer function of the sampling filter is folded or convoluted with the sampled signal in the computer. That procedure is possible only if sampling was effected correctly. In contrast in the event of sub-sampling the error is further increased.

Between the upper signal frequency fs, the sampling frequency fa, the asymptotic steepness or order of the sampling filter N and the over-sampling factor k, there is the following relationship, in relation to the achievable degree of accuracy or resolution A in bits:

$$k = \frac{\ln(fa) - \ln(fs)}{\ln(2)} - 1$$

$$A = k * N + 1$$

For a limit frequency of fs=2 Hz with a degree of resolution of A=13 bits, that gives for example the following possible configurations:

First-order filter (N=1)→sampling frequency fa=16384 Hz

Third-order filter (N=3)→sampling frequency fa=64 Hz

Sixth-order filter (N=6)→sampling frequency fa=16 Hz.

The last combination is the arrangement used in our embodiments. In the case of low-order filters with 'good-natured' performance in respect of the transfer function, we must surprisingly reckon on extreme over-sampling rates in order to attain usable results. In spite of the high sampling frequency of over 16 kHz, only the spectral components up to 2 Hz are correctly sampled (at A=16 bits, fs=20 kHz and fa=44 kHz filters of the 109th order would be necessary in order to effect sampling in accordance with the sampling theorem).

Over-sampling has a further advantage: even if each analog-digital converter is ideal in respect of its characteristic, it adds the quantisation noise to the signal to be sampled so that the signal is falsified not only by the quantisation operation, that is to say discretisation of the amplitude values, but it is also additionally caused to have noise.

The noise can approximately be considered as white so that, with a larger sampling band width, that is to say with over-sampling correspondingly less noise falls into the signal band width and thus the signal-noise ratio of the converter but not the signal can be proportionally improved.

The 6th-order sampling low pass filter used is provided by the series connection of two third-order low pass filters (asymptotic edge steepness 18 dB/octave or 60 dB per decade). Each low pass filter comprises an operational amplifier connected as a voltage follower, and an R-C-circuit.

The amplitude, phase and envelope curve distortions due to the frequency and phase characteristics of all filters as well as the group delay or transit times can be reversed by a procedure whereby the time function is folded or convoluted with its inverse transfer function T−1 (w) of the preceding signal path T (w) and thus complete pole-zero location compensation is effected. That can be necessary if the original time signal is to be reconstructed and therefore deformation of the time signal by the converters and the elements of the transmission chain must be avoided. In a situation of use in which the significant detection of a spectral line is required, it is possible to disregard that.

In the structure according to the invention, in one embodiment, the time signal passes from the converter (receiving antenna) to the personal computer (A/D converter) through at least one fifteenth-order high pass filter and a twenty first-order low pass filter which arise out of the product of the transfer functions of the individual elements of the measurement chain (direct mixer, pre-amplifier, 2*low-pass filter, 2*high-pass filter, A/D converter).

If necessary the dynamic behaviour of the analog part of the electronic system can also be improved by units which directly effect pole-zero location compensation. By virtue thereof, it is possible to reduce noise, an unfavourable transmission characteristic can be improved, or optimum transmission properties can be achieved, in accordance with given criteria.

3. High-pass filter

In accordance with the invention spectral limitation of the input signal, with respect to the low frequencies, is desirable for three reasons:

1. 1/f-noise

The amplitude of the 1/f noise increases reciprocally relative to frequency. Therefore, with an increasing measurement time, noise components occur at a lower and lower frequency and falsify the signal to be measured. The main sources for the 1/f noise are the transmission oscillator, the converter oscillator and the operational amplifiers.

2. Slow movements

At a constant speed movements of the body to be detected result in a Doppler frequency shift and thus spectral components which can fall into the frequency band to be investigated. A wide additional band occurs, in the event of irregular movements. The slower the movements, the lower the frequency of the spectra which are then more and more difficult to separate from noise components.

3. Evaluation time

In order to identify a spectral line of the frequency f, measurement must be effected at least for a time t=1/f, that is to say, the lower the frequencies to be detected, the longer the period for which measurements must be made. As it is not possible to guarantee that the measurement time is an integral multiple of the spectral component which is of interest, a leakage effect occurs in the Fourier analysis. That results in spectral spreading. Therefore, when analysing low frequencies, it is necessary to observe a measurement time which is a multiple of the period duration, in which case the degree of accuracy increases proportionally with the measurement time. With 10% errors in the spectral resolution and 0.2 Hz lower frequency it is necessary to reckon on a measurement time of typically 50 seconds.

Figure 3:
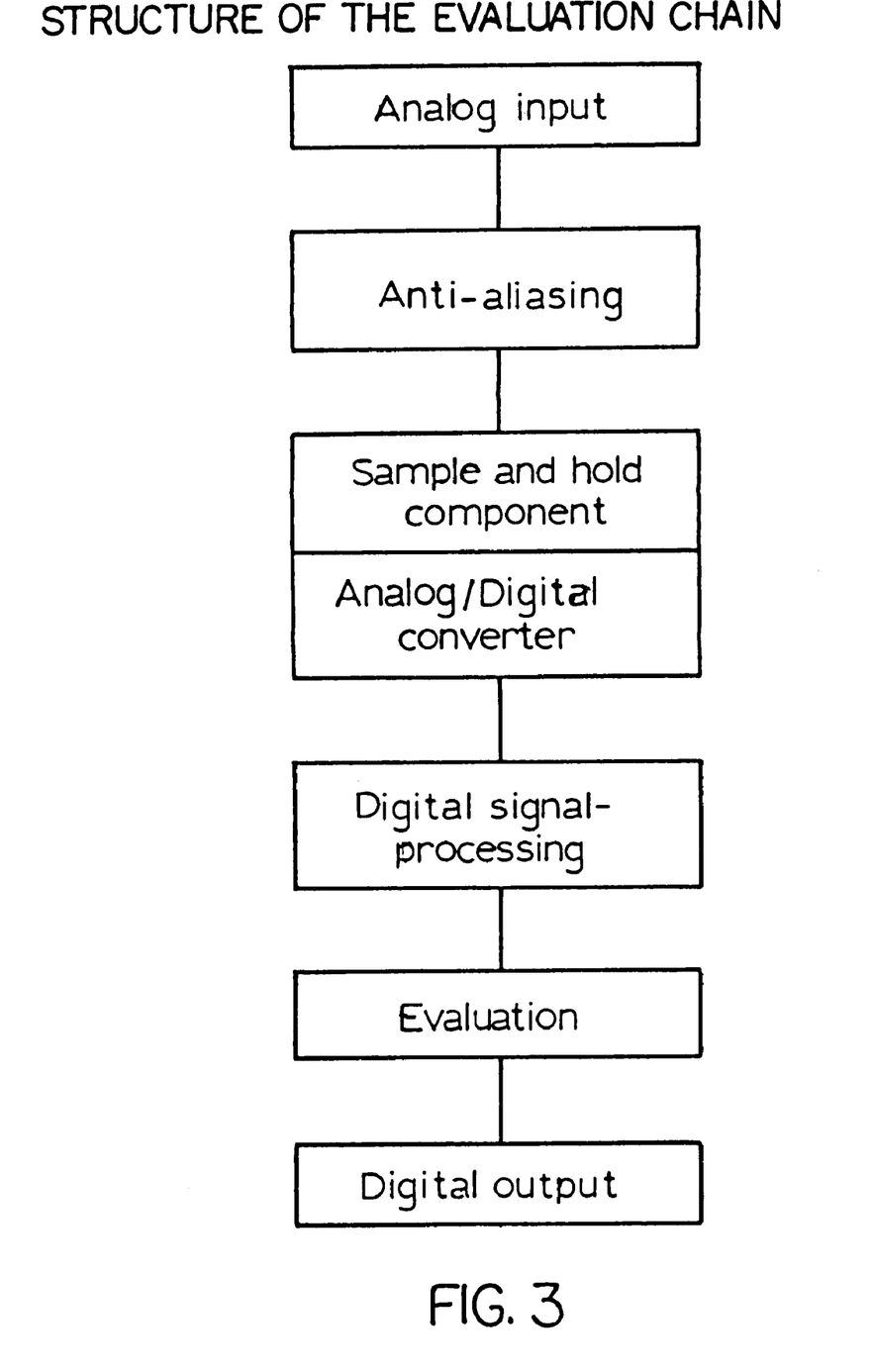
FIG. 3 is a diagrammatic view of the structure of the evaluation chain.

FIG. 3 shows the general structure of the evaluation chain. Personal computers from the office sector, IBM-PC-compatible type, are used as central units, as the power thereof is adequate for the task involved.

Figure 4A:
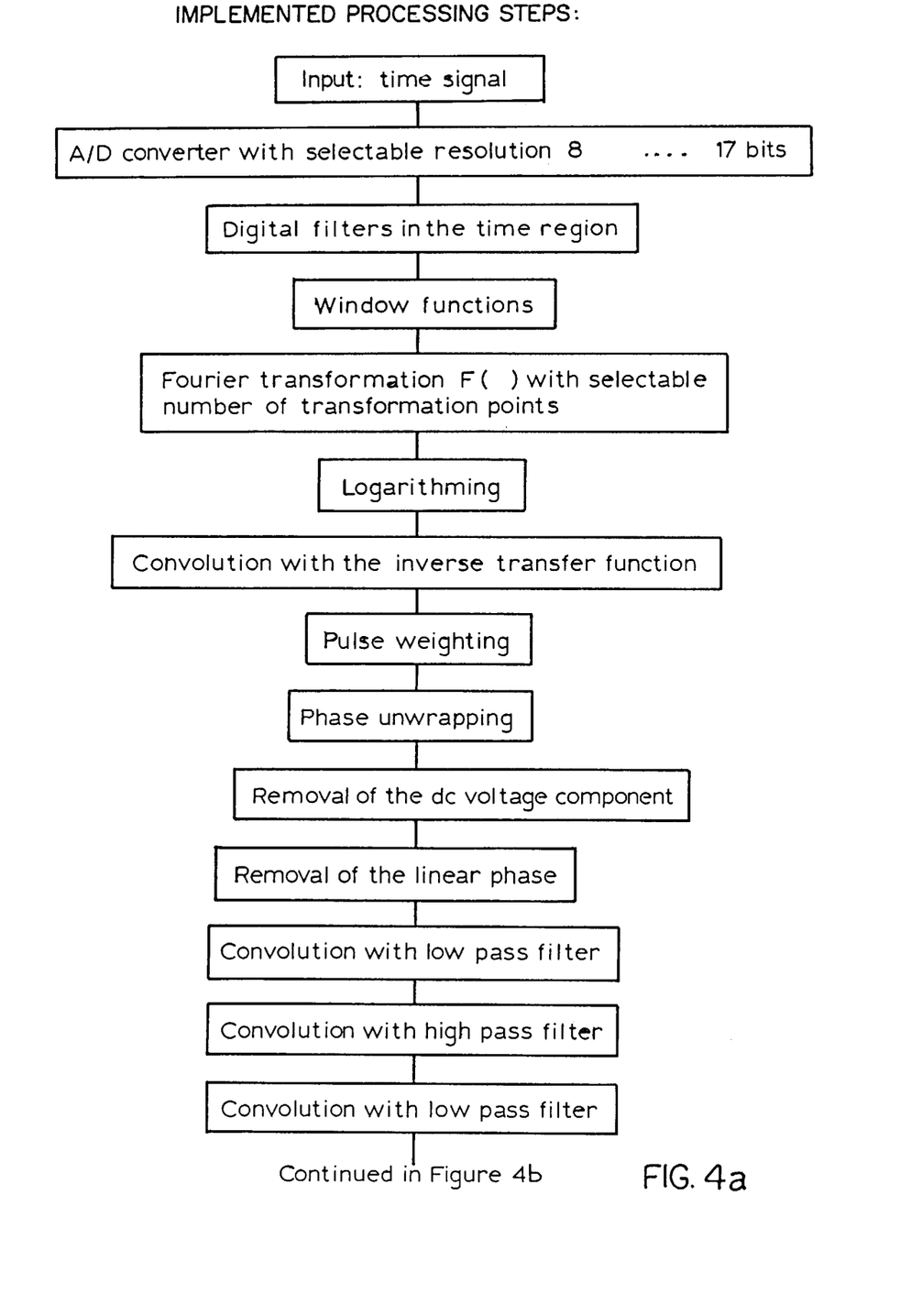
FIGS. 4 and 4a show a flow chart of the implemented processing steps.
Figure 4B:
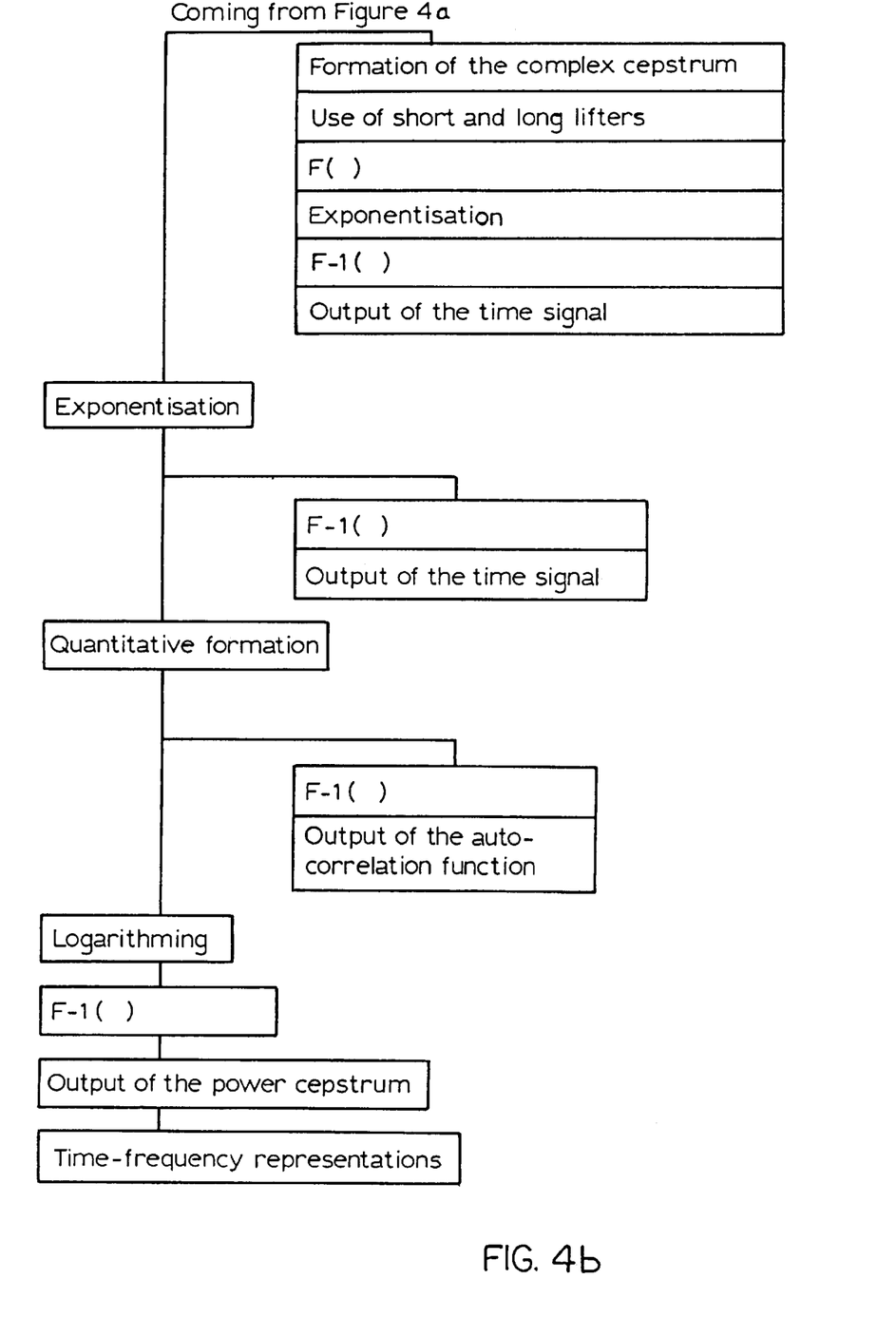

The plan shown in FIGS. 4 and 4a gives an overview of the implemented processing steps, therein F{ } denotes the Fourier transformation and F−1{ } denotes the inverse Fourier transformation.

RESULTS

After various preliminary tests a sampling rate of 16 Hz with a unipolar resolution of 13 bits (total resolution 14 bits) was found to be well suited. The window width selected for spectral analysis was 512 values, corresponding to about 33 seconds: the Hamming window was selected as the window.

Figure 5:
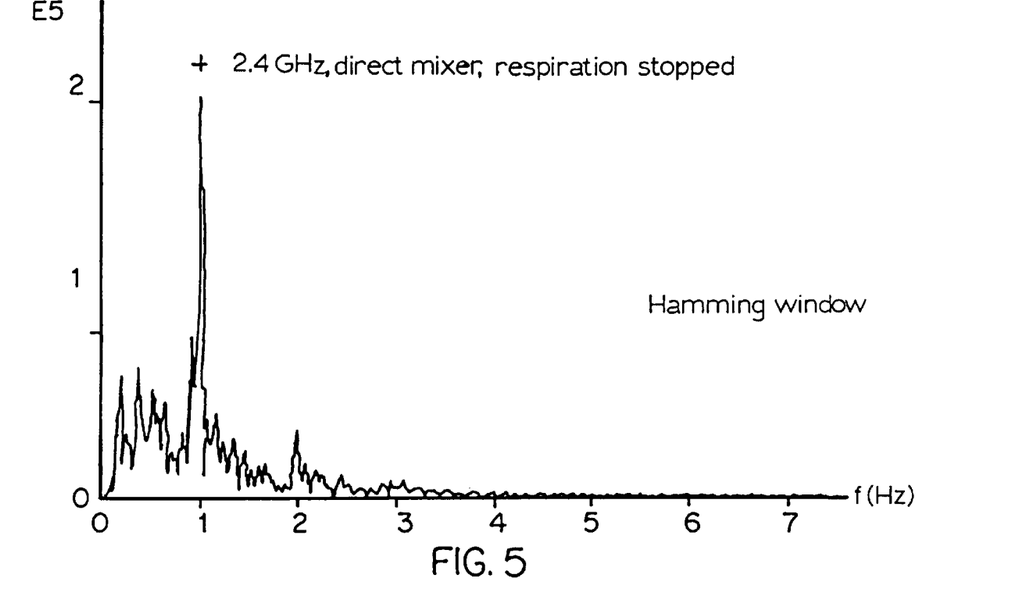
FIGS. 5 and 6 are spectral representations of electromagnetic signals detected with the apparatus according to the invention, with frequency components which are characteristic of the vital functions of human living bodies.

FIG. 5 shows the heart rate of a test person with respiration stopped. The spectral component stands out so clearly from the surroundings that further processing is not necessary to detect the heartbeat of the test person. The quantitative spectrum is plotted in any units, in relation to frequency in Hertz. Measurement was effected at 2.4 GHz, the diode direct receiver, that is to say the ½-dipole, was used as the receiver, the local oscillator was used as the transmitter, respiration was stopped.

Figure 6:
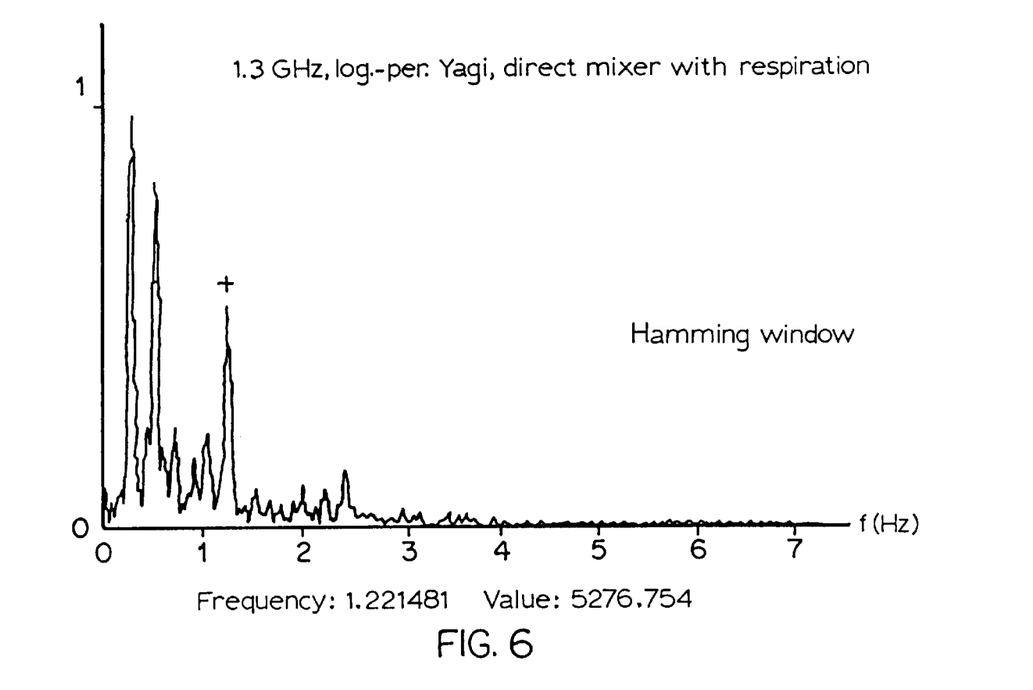

FIG. 6 shows the spectrum of the signal reflected by a breathing person, using the diode direct receiver and the logarithmic-periodic Yagi antenna and the 1.3 GHz transmitting oscillator as the source. Both heart rate and also respiration rate are present At the frequency of 440 MHz, the tests were found to be difficult, because of the extreme sensitivity of the entire arrangement. Almost all test recordings exhibited overdriving phenomena and reactions to external events.

The problem of overdriving can be resolved by suitable attenuation; detection of respiration and cardiac activity is not influenced thereby.

If a circulator is used, then, as described, it is possible just to use an antenna which transmits and receives simultaneously.

The examples clearly demonstrate that the detection of living people is possible. In that respect neither walls nor distances of some 10 meters are an obstacle worth mentioning. Working frequencies of 1.3 GHz and 2.4 GHz were found to be highly suitable. When using antennae which are still manageable, the level of sensitivity is sufficiently high to achieve reproducible results with clear identification of the heartbeat and respiration without intensive numerical processing steps being necessary, as suitably strong reception signals are already present.

Circuit diagram high-pass and anti-aliasing low-pass filters

Figure 8A:
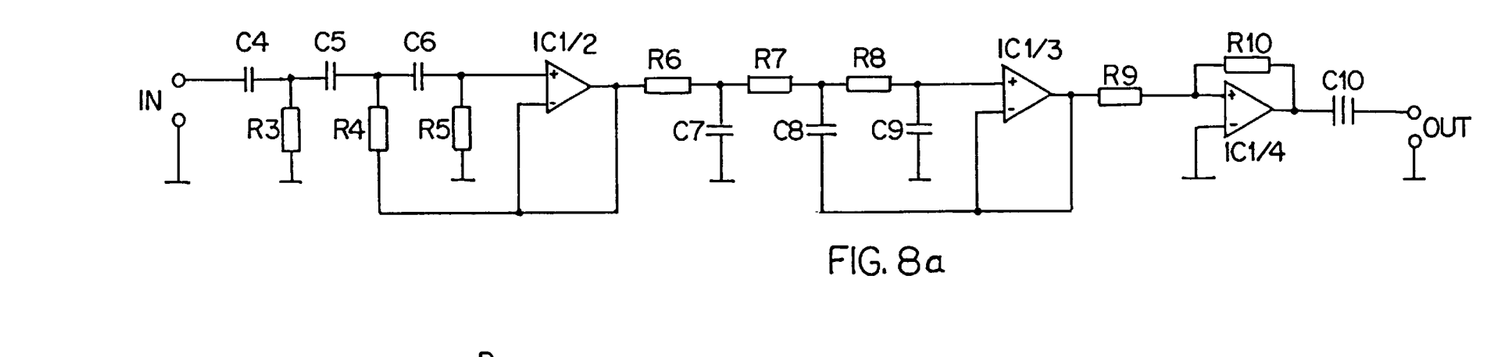
FIG. 8a shows a circuit diagram of an analog high pass filter and an anti-aliasing filter in the form of a low pass filter.
Figure 8B:
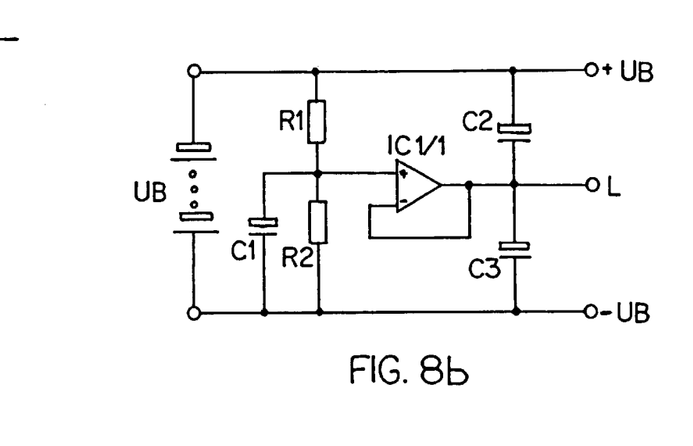
FIG. 8b shows a circuit diagram of voltage symmetrising.

The circuit diagram of the unit employed for band restriction is shown in FIGS. 8a and 8b. The third-order high pass filter suppresses the low-frequency noise components, in particular the 1/f noise. The following third-order low-pass filter limits the spectrum to higher frequencies. There then follows a linear amplifier stage for level matching. The operating voltage is electronically symmetrised so that a unipolar supply is sufficient. Two of those units in cascade relationship fulfil the requirements set by the sampling theorem.

Diode demodulator circuit diagram

A diode detector whose circuitry is shown in FIG. 7 serves for phase demodulation of the reception signal which is mixed on to the intermediate frequency and as a direct demodulator for the developed receiver antennae. The circuitry corresponds to a typical power meter; a pre-conduction or input current can be impressed from the output. The input impedance can be adapted to the IF-mixer or the antennae.

Diode direct receiver circuit diagram

The diode direct receivers comprise diode detectors which are ½ or 1 wavelength long and which are multiplied by the corresponding shortening factor and are suitably connected upstream. A pre-conduction or input current can be impressed at the output.

In addition each unit is provided with its own stabilised voltage supply and its own on-off switch so that units with a long time constant (local oscillators, pre-amplifiers, low-pass filter) could be operated in continuous duty and were in thermal and electrical equilibrium while consumers or loads with a high current consumption (final transmitting stages, converters) can be switched off between uses.

Preferred embodiments of the invention are described hereinafter.

Figures 9, 10:
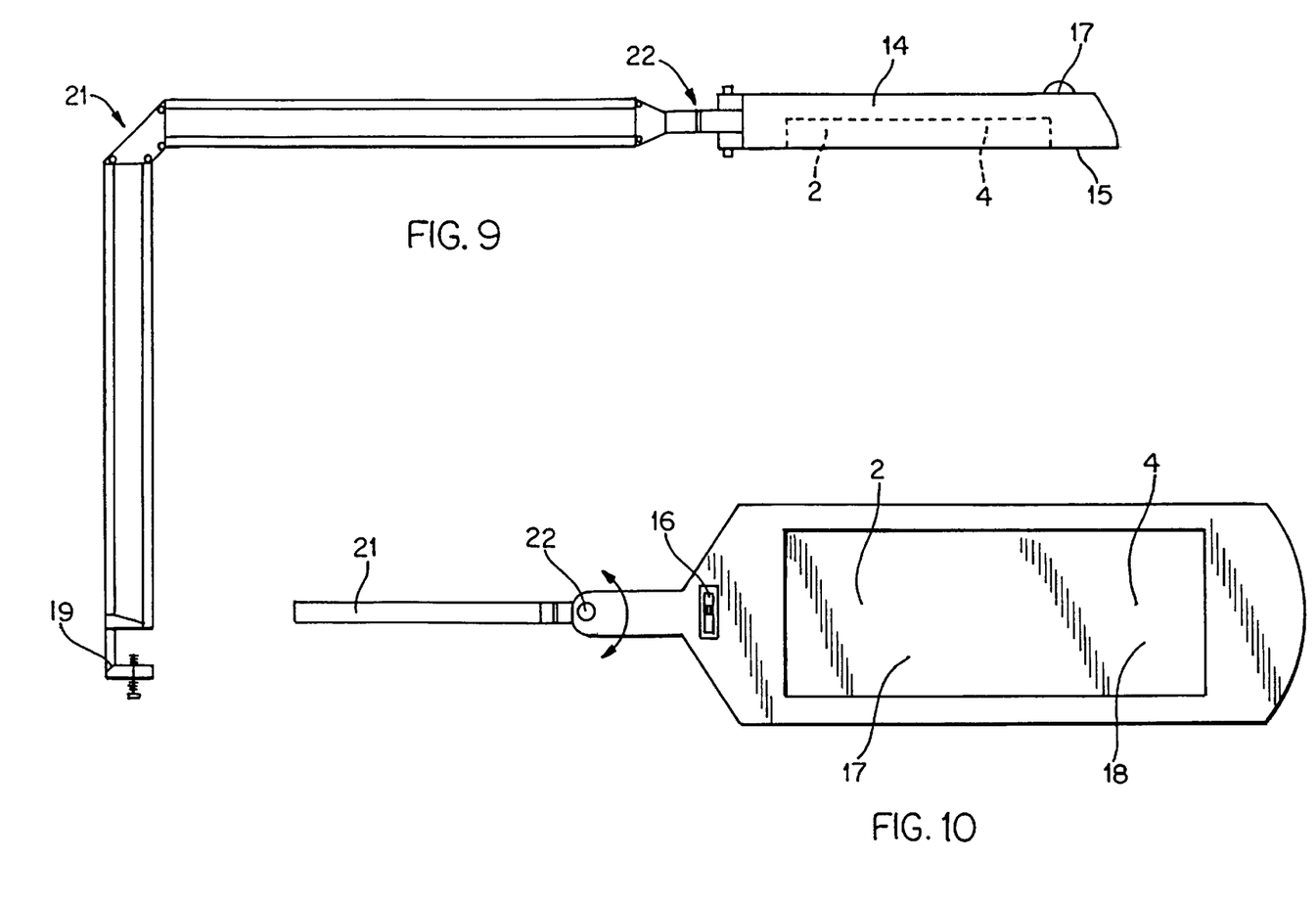
FIG. 9 is a view of a first embodiment according to the invention for monitoring vital functions, viewed from the side.
FIG. 10 is a view of the head of the embodiment illustrated in FIG. 9, from below.

A first embodiment according to the invention includes a system for monitoring the vital function of respiration and/or heartbeat in the medical sector. Disposed in a housing 14 are the transmission antenna 2 and the receiving antenna 4 with their respective associated reflectors. The antenna 2 which is used as the transmission antenna is connected to a transmitter 1 which outputs a power of 20 mW as a substitute or equivalent load of real 377 Ω.

The horizontal and vertical aperture angles of the antennae are adapted to the respective use involved. For monitoring in intensive care units, at least the reception antenna has a reception characteristic which has small secondary lobes and whose main detection area is approximately of the size of a human thorax. The receiving antenna 4, Rx is connected to a receiver which, by means of the converter 6, converts the incoming signals into the above-described frequency range. That is then followed by the demodulator 5, the amplifier, the filter 7 and a driver for signal transmission.

The signals are fed to the remotely disposed analog/digital converter 9 by means of the screened lines (not shown). The analog/digital converter 9 and the further above-described electronic evaluation system are disposed either in a portable unit, preferably in a small suitcase, or in a static mains-powered item of equipment, or they are part of a central monitoring unit with central display of the vital functions in the form of the spectra shown in FIGS. 5 and 6, in a clinical monitoring station. In order to make the signals correctly evaluatable in the time region, convolution is effected with the inverse transfer function of the signal path which is disposed upstream of the analog/digital conversion operation. Thus, the substantially instantaneous condition of the vital functions or, with suitable image storage devices, the history thereof, can be represented on monitors of the central monitoring station or the portable unit.

In a simpler embodiment as shown in FIG. 10 the front plate 15 carries an on/off switch 16 and an optical indicator 17 and/or an acoustic indicator 18. The optical indicator 17 can be arranged beneath a transparent part of the front panel 15, as shown in FIG. 10, or above the housing 15, as shown in FIG. 9. By means of a clamping connection 19 which is only diagrammatically shown in FIG. 9 in the form of a screw clamping device, this first embodiment according to the invention can be quickly and easily fixed to or in the vicinity of beds of patients who are to be monitored. Moreover, it is in accordance with the invention for the fixing device 19 used to be any other known alternative constructions such as for example mechanical coupling arrangements or a bayonet arrangement with the respective stationarily mounted co-operating member. In that way, the apparatus can be fixed to or in the vicinity of the bed of the person to be monitored, in an at-home situation.

A hinge arm 21 together with the rotary pivot joint 22 at the end of the arm 21 permits controlled orientation of the apparatus in per se known manner.

Figure 11:
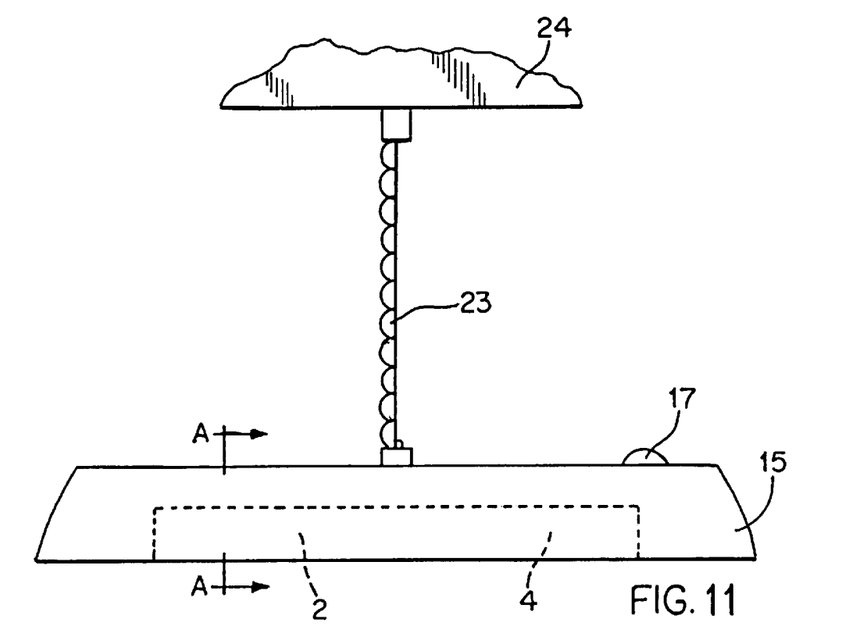
FIG. 11 shows a second embodiment according to the invention for stationary mounting, viewed from the side.
Figure 12:
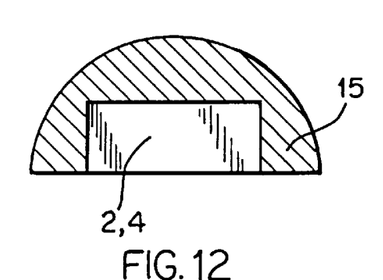
FIG. 12 is a sectional view taken along line A—A in FIG. 11 through the second embodiment according to the invention.

In a further embodiment as illustrated in FIG. 11, the housing 15 is fixed approximately centrally with a pull or tie device 23 to a ceiling 24 of a building. The device 23 permits adjusting in respect of height and in particular permits the housing 15 to be moved downwardly so that a person lying under the apparatus can be detected in the optimum fashion, while when the apparatus is displaced upwardly, there is no impediment in terms of freedom of movement.

In order reliably to take account of the clinical factors involved, the detected band width of the frequencies is limited to a range of 0.02 Hz through 6 Hz. In that way, respiration periods of 166 ms through 50 s and pulse rates of 1.2 through 360 beats per minute can be detected. An electronic evaluation system disposed at a downstream location detects the height of the spectrally limited signal and has a threshold value setting which, in the event of the absence of the signals which provide warning for the vital functions, sets off an optical and/or acoustic alarm or which, upon being integrated into a monitoring system, transmits the alarm condition to that system.

In another alternative configuration the detectable respiration periods are limited to less than 30 s so that the period to evaluation of the signals is also not longer than somewhat over 30 s.

The main areas of use of the above-described embodiments concern the monitoring of people who are in danger of committing suicide, cable-free monitoring of comatose people and people with burns injuries. In clinical situations and at home, it is possible to provide for monitoring people who are in need of care and who are in need of intensive care, while in relation to small children, it is possible to provide for monitoring in regard to the absence of the vital functions, in order to prevent sudden death of the child. Sleep disturbances which are known from intensive care units and which are caused by the cable arrangements can be alleviated and in part even eliminated as, besides the purely mechanical obstruction and hindrance, the psychological strain also decreases.

It is also possible to detect the cardiac rate of the unborn child, in the case of pregnancy investigations. That also makes it possible to provide for trouble-free and uninterrupted continuous monitoring, without the electrodes which conventionally have to be fitted.

Figure 13:
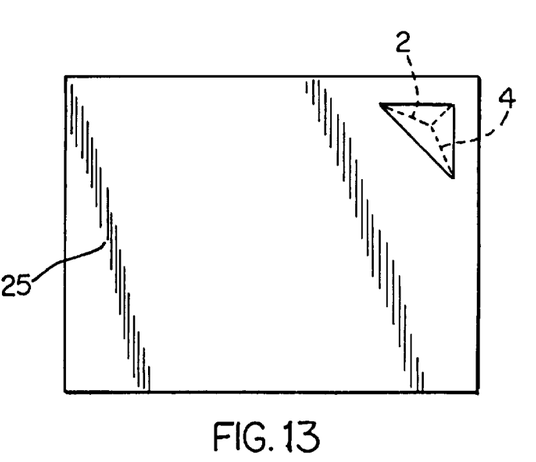
FIG. 13 shows a third embodiment according to the invention for room monitoring.

In a further embodiment according to the invention, as shown in FIG. 13, a room 25 is monitored by means of a transmitting/receiving device disposed in one corner of the ceiling. As described in connection with the preceding embodiments, the transmission antenna 2 and the receiving antenna 4 are connected to the above-described electronic units for signal evaluation purposes.

The transmitter 1 preferably transmits in the frequency range of between 300 MHz and 3 GHz, and it outputs a power of between some mW and several W at a substitute or equivalent load of real 50 Ω or real 377 Ω. In the case of room monitoring the antennae 2, 4 are in the form of tripole prisms, as shown in FIG. 13.

Figure 14:
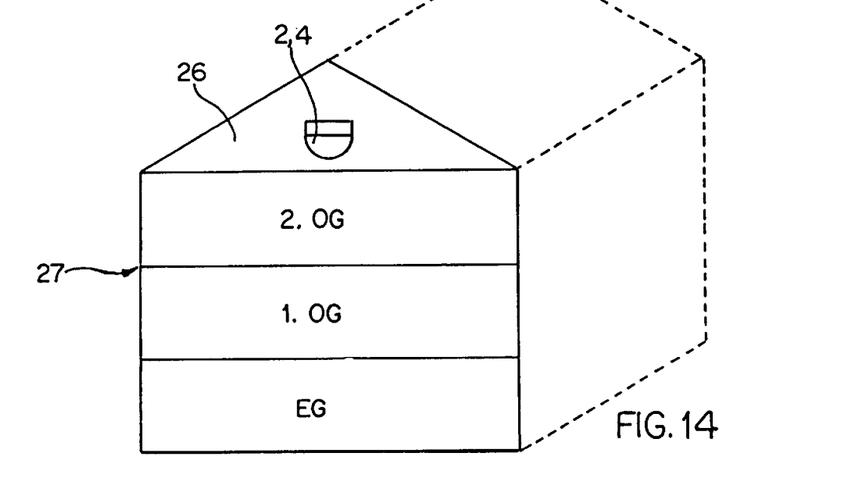
FIG. 14 shows an alternative of the arrangement shown in FIG. 13 for monitoring a plurality of building storeys.

In the further embodiment shown in FIG. 14, a circularly polarising transmitting/receiving antenna 2, 4 is arranged in the top floor 26 of the building 27. By virtue of the appropriate configuration of the spatial transmission characteristic of the transmitting antenna 2 and the spatial receiving characteristic of the antenna 4, they are adapted to the desired detection area, in general the dimensions of the building to be monitored. It is also possible to arrange a plurality of transmitting antennae 2 and a plurality of receiving antennae 4 in the regions to be monitored, and for each to be connected to the electronic evaluation system.

Figure 15:
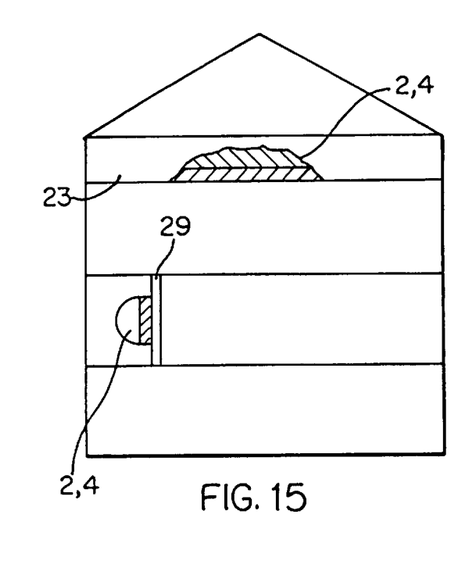
FIG. 15 shows a further arrangement for room and/or building monitoring.

In the embodiment shown in FIG. 15 the transmitting or the receiving antenna 2, 4 are arranged behind a suspended ceiling 28. The large-area extent of the antennae simplifies accurate definition of the detection area. FIG. 15 also shows a further concealed monitoring arrangement, in the region of the side wall 29.

Figure 16:
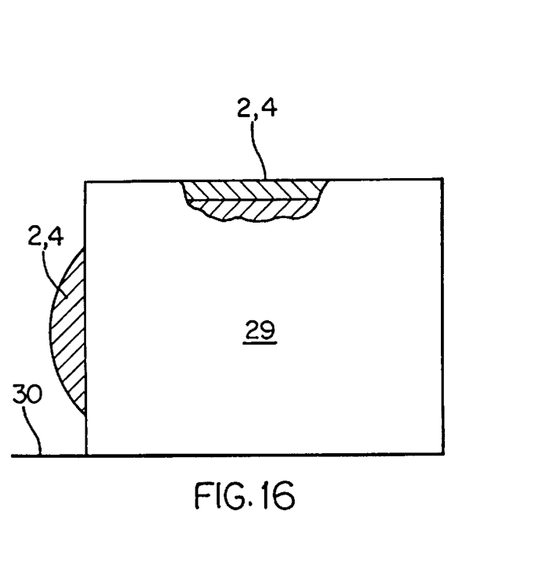
FIG. 16 shows a still further arrangement for room monitoring and monitoring the area in front of buildings.

FIG. 16, in addition to monitoring of the room 30, also shows a transmitting/receiving antenna combination 2, 4 for monitoring the area in front of a building. In this case the region 30 which is only diagrammatically illustrated can be a forecourt of a private and a public building. Thus for example uninterrupted monitoring, such as to cover an entire surface, is possible in a psychiatry situation or in a penal detention situation. In addition, a subsequently connected electronic evaluation system can perform automatic signalling, as described hereinbefore in regard to the medical areas of use.

Further important areas of use are in the sector of the chemical industry and in relation to installations, which are exposed to radiation, of the nuclear energy suppliers or nuclear fuel producers and processors. Regions which are exposed to radiation or the effects of chemicals can be monitored in such a way that an entire surface is covered thereby, so that people can enter those areas, without triggering an alarm, only if they have been suitably made known, or, in the event of dangerous substances escaping, the presence of living people in the vicinity of the location at which the substances have escaped can be detected.

A further essential use lies in the area of combatting fire in a controlled and specific manner. Wherever oxygen-binding extinguishing agents or special extinguishing procedures for combatting fire are used instead of conventional agents or procedures in order to avoid major property damage (for example in the case of a fire in the printing and computer industry), then, in order not to endanger the lives of people still in the buildings, the fire-extinguishing procedure may begin only when the locations of the fire have been checked to ascertain whether living people are present there. That monitoring effect is prescribed by statute law for the use of specific fire-extinguishing agents, but it is highly controversial, because of the disadvantages that it involves in regard to life and limb of the fire services. Checking of the fire locations for any people who may still be alive on the other hand can be effected efficiently, speedily and from the exterior, that is to say also from outside the premises which are on fire.

Thus, any people in the premises which are on fire are detected more quickly, rescued more speedily and the fire services are less in danger at the source of the fire. The extent of fire damage can additionally be generally minimised by virtue of the fire-extinguishing procedure beginning are quickly.

I claim:

1. Apparatus for detecting vital functions of living bodies by detecting electromagnetic signals comprising a receiving device for receiving electromagnetic signals from living bodies, wherein the receiving device (3) for receiving electromagnetic signals includes a device for obtaining frequency components that are characteristic of the living bodies, out of the received electromagnetic signals, wherein the receiving device (3) includes a direct demodulator (5) that has a non-linear current/voltage characteristic that is frequency-selective for demodulation of frequency components that are characteristic of the living bodies.

2. Apparatus as set forth in claim 1 characterized in that the direct demodulator demodulates frequency components which are characteristic of vital functions of living bodies directly out of the received electromagnetic signals.

3. Apparatus as set forth in claim 2 characterized in that the direct demodulator (3) includes one of a diode, a bipolar and a field effect transistor as the frequency-selective element.

4. Apparatus as set forth in claim 1 characterized in that the receiving device (3) includes a frequency conversion device (6) connected ahead of the demodulator (5) in a direction in which the electromagnetic signals are received.

5. Apparatus as set forth in claim 1 characterized in that the apparatus includes a transmission device (1) transmitting of an electromagnetic carrier signal at a fixed frequency.

6. Apparatus as set forth in claim 5 characterized in that the carrier signal is in a frequency range of approximately one MHz to approximately one THz.

7. Apparatus as set forth in claim 1 characterized in that the device for obtaining frequency components which are characteristic of the living bodies includes a filter device (7), a sampling device, an A/D converter (9) and a computing device (10) for spectral analysis.

8. Apparatus as set forth in claim 7 characterised in that the filter device (7) includes at least one analog sampling filter.

9. Apparatus as set forth in claim 8 characterised in that the sampling filter limits the band width of the electromagnetic signal towards high frequencies prior to the sampling operation and prior to the A/D conversion operation.

10. Apparatus as set forth in claim 1 characterized in that the apparatus further includes a transmission antenna (2) for transmitting an electromagnetic carrier signal, and the receiving device comprises a receiving antenna (4) wherein the transmission and receiving antenna are held in a common housing (14) for pivoting and nutating movement with a releasably fixable holder (19).

11. Apparatus as set forth in claim 1 characterized in that the apparatus further includes a transmission antenna (2) for transmitting an electromagnetic carrier signal and the receiving device comprises a receiving antenna (4) wherein the transmission and receiving antenna are mounted in a common housing (14) which is fixed to a ceiling (24) by way of a holder (23) which is adjustable in respect of height.

12. Use of an apparatus as set forth in claim 1 further including positioning means for positioning the apparatus to allow for contact-free monitoring of the vital functions of intensive care patients.

13. Use of an apparatus as set forth in claim 1 further including positioning means for positioning the apparatus to allow for monitoring one of small children and apnoea patients for at least one of cardiac and respiratory arrest.

14. Use of an apparatus as set forth in claim 1 further including positioning means for positioning the apparatus to allow for monitoring the state of inmates in places of detention.

15. Use of an apparatus as set forth in claim 1 further including positioning means for positioning the apparatus to allow for at least one of monitoring and safeguarding at least one of rooms, buildings and open land surrounding same.

16. A method for detecting vital functions of living bodies by detecting electromagnetic signals comprising receiving electromagnetic signals from living bodies and obtaining frequency components which are characteristic of the living bodies from the received electromagnetic signals by directly demodulating the received electromagnetic signals by a direct demodulator having a non-linear current/voltage characteristic that is frequency-selective for demodulation of frequency components that are characteristic of the living bodies.

17. The method as set forth in claim 16 further characterized by converting the received electromagnetic signals to an intermediate frequency between high and low frequencies.

18. The method as set forth in claim 16 further characterized by limiting the received electromagnetic signals with an analog device towards high and low frequencies.

19. The method as set forth in claim 18 further characterized by transforming the digital signals from a time region into a frequency region and then evaluating and representing the digital signals as output signals.

20. The method as set forth in claim 19 further characterized by analyzing the transformed signals in a frequency range of from about 0.01 Hz through about 10 Hz for frequency components of at least one of cardiac and respiratory activity, which are characteristic of vital functions of living bodies.

21. The method as set forth in claim 20 further characterized by analyzing the transformed signals in a frequency range between about 0.02 Hz and about 3 Hz.

22. The method as set forth in claim 16 further characterized by filtering, sampling, and converting the received electromagnetic signals into digital signals.

23. The method according to claim 22 further characterized by folding the digital signals with a window function in a time region and with an inverse transfer function of a receiving device.

24. The method as set forth in claim 16 wherein the step of obtaining frequency components which are characteristic of the living bodies further includes contact-free monitoring of the vital functions of intensive care patients.

25. The method as set forth in claim 16 wherein the step of obtaining frequency components which are characteristic of the living bodies further includes monitoring at least one of small children and apnea patients for at least one of cardiac and respiratory arrest.

26. The method as set forth in claim 16 wherein the step of obtaining frequency components which are characteristic of the living bodies further includes monitoring the state of inmates in places of detention.

27. The method as set forth in claim 16 wherein the step of obtaining frequency components which are characteristic of the living bodies further includes at least one of monitoring and safeguarding at least one of rooms, buildings, and open land surrounding same.

* * * * *